[19] United States Patent
Jacobs et al.

[11] Patent Number: 4,851,402
[45] Date of Patent: Jul. 25, 1989

[54] ESTRIOL GROWTH PROMOTANT

[75] Inventors: Martin J. Jacobs, Terre Haute, Ind.; John Katzenellenbogen, Urbana, Ill.

[73] Assignee: International Minerals & Chemical Corp., Northbrook, Ill.

[21] Appl. No.: 19,935

[22] Filed: Feb. 27, 1987

[51] Int. Cl.$^4$ .................... C07J 1/00; A61K 31/565
[52] U.S. Cl. .................................................. 514/182
[58] Field of Search ........................................ 514/182

[56] References Cited

U.S. PATENT DOCUMENTS

| | | | |
|---|---|---|---|
| 2,394,628 | 2/1946 | Meyer | 167/74 |
| 2,751,303 | 6/1956 | Burroughs | 99/2 |
| 3,041,173 | 5/1962 | Burroughs | 99/2 |
| 3,115,440 | 12/1963 | Ercoli | 167/74 |
| 3,121,042 | 2/1964 | Ercoli | 167/74 |
| 3,166,473 | 1/1965 | Mochida | 167/58 |
| 3,235,454 | 2/1966 | Mattox | 167/53 |
| 3,410,874 | 11/1968 | Birch | 260/345 |
| 3,436,390 | 4/1969 | Lefebvre | 239/57 |
| 3,729,560 | 4/1973 | Hagerman | 424/238 |
| 3,919,420 | 11/1975 | Grandadam | 424/240 |
| 4,212,864 | 7/1980 | Tax | 424/243 |
| 4,738,957 | 4/1988 | Laurent | 514/182 |

OTHER PUBLICATIONS

Preston et al., *J. Animal Sci.*, vol. 46, No. 2, 541(1978).

*Primary Examiner*—Mark L. Berch
*Attorney, Agent, or Firm*—Wendell Ray Guffey; Thomas L. Farquer

[57] ABSTRACT

Estriol is administered to ruminants in dosages from about 0.01–4.0 mg/ruminant/day to promote growth and increase feed utilization efficiency.

16 Claims, No Drawings

ESTRIOL GROWTH PROMOTANT

This invention relates generally to methods for promoting growth in animals and particularly to a method for using estriol to promote growth and increase feed utilization efficiency in ruminants.

BACKGROUND OF THE INVENTION

17β-Estradiol, Estra-1,3,5,(10)-triene-3,17β-diol, is a naturally occurring estrogen in mammals which is formed by the ovary, placenta, testes and possibly the adrenal cortex. 17β-Estradiol is reported to promote growth and increase feed utilization efficiency. However, estriol and estrone, the weakly estrogenic metabolites of 17β-estradiol, were reported not to promote growth or increase feed utilization efficiency. Preston et al., *J. Am. Sci.*, Vol. 46, No.2, 541 (1978).

Estriol, Estra-1,3,5(10)-triene-3,16α,17β-triol, is a metabolite of 17β-estradiol. Estriol has been isolated from: Urine as disclosed in Marrian, *Biochem. J.*, 23:1233 (1929); Placenta as disclosed in Collip et al, *Endocrinology*, 18:71 (1934); and Plants as disclosed in Skarzynski, *Nature*, 131:766 (1933). Estriol's structure was disclosed in Huffman, et al., *J. Am. Chem. Soc.*, 69:1835 (1947). Estriol is synthesized according to the methods disclosed in Huffman et al., *J. Am. Chem. Soc.*, 71:719 (1940) and Leeds et al., *J. Am. Chem. Soc.*, 76:2943 (1954).

U.S. Pat. No. 4,078,060 to Benson et al discloses using estrogen derivatives to induce an estrogenic response in patients. U.S. Pat. No. 2,751,313 discloses oral growth promoting compositions of several estrogenic agents and their use in promoting growth and increasing feed utilization efficiency in ruminant animals. U.S. Pat. No. 3,041,173 discloses the use of estrogenic agents in combination with other agents for enhancing growth in animals. U.S. Pat. No. 2,751,303 discloses the oral administration of estrogenic substances to promote growth in meat-producing animals. Useful estrogens include stilbestrol, 17β-estradiol, derivatives of stilbestrol, estrone, dianisylhexene, genistein, dienstrol, and hexestrol. U.S. Pat. No. 3,235,454 discloses using long chain hydrocarbon aliphatic carboxylic acid esters of 17β-estradiol for improving meat production in meat-producing animals. U.S. Pat. No. 3,729,560 discloses using estriol for treating hair and scalp. U.S. Pat. No. 3,166,473 discloses using esters of estriol for treating vaginitis, cervicitis, climacteric disturbance, menorrhagia and for shortening labor and facilitating delivery.

Estrogens such as 17β-estradiol and diethylstibestrol are a group of biologically active compounds which are used in animals as growth promotants. In recent years, however, methods for promoting growth in animals, particularly ruminants such as sheep and cattle, using estrogens have been criticized because of the alleged adverse side effects caused by the compounds. These estrogenic compounds have been reported to induce excessive sexual stimulation of animals, including mammary development and lactation as well as other undesirable physiological side effects on the reproductive system. Methods for promoting growth and increasing feed utilization efficiency using new or known compounds which do not cause significant undesirable estrogenic side effects are therefore needed.

SUMMARY OF THE INVENTION

It is, therefore, an object of the present invention to provide a method for promoting growth in ruminants.

It is another object of the present invention to provide a method for increasing feed utilization efficiency in ruminants.

It is a further object of the present invention to provide a composition for promoting growth and increasing feed utilization efficiency in ruminants.

These and other objects are achieved by administering the known compound estriol to ruminants in amounts sufficient to promote growth and increase feed utilization efficiency. Estriol is administered alone or in a composition comprising estriol and a pharmaceutically acceptable carrier. Estriol can be administered to the ruminants in any acceptable manner including orally, by injection, using an implant, and the like.

In the preferred embodiment, estriol is administered to ruminants in dosages from about 0.01–4.0 mg/ruminant/day to promote growth and increase feed utilization efficiency.

Other objects, advantages, and novel features of the present invention will become apparent from the following detailed description of the invention.

DETAILED DESCRIPTION OF THE INVENTION

According to the present invention, estriol is administered to ruminants in amounts sufficient to promote growth and increase feed utilization efficiency.

Although the dosages of estriol vary according to the age, size, and character of the particular ruminant, estriol is typically administered to the ruminant in dosages from about 0.01–4.0 mg/ruminant/day, preferably from about 0.05–2.0 mg/ruminant/day.

Estriol according to the present invention can be administered to the ruminants in any acceptable manner including orally, by injection, using an implant, and the like. Injections and implants are preferred because they permit precise control of the timing and dosage levels used for administration. Estriol according to the present invention is preferably administered parenterally. As used herein, parenteral administration means administration by intravenous, intramuscular, subcutaneous, or intraperitoneal injection, or by subcutaneous implant.

Estriol according to the present invention can be administered orally to the ruminant. Oral administration includes administering estriol in tablets, suspensions, solutions, emulsions, capsules, powders, syrups, feed compositions, and the like. For example, estriol can be blended with ordinary feed compositions in amounts sufficient to promote growth and increase feed utilization efficiency in ruminants.

When estriol is to be administered in feeds, a feed composition may be prepared containing the usual nutritionally-balanced feed containing quantities of carbohydrates, proteins, vitamins and minerals, together with estriol in accordance with the present invention. Some of the usual dietary elements included in feed compositions are grains, such as ground grain and grain by-products, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. Examples of well known feed compositions useful in the present invention include: U.S. Pat. No. 4,283,400 discloses a medicated animal feed composition based on liver meal. U.S. Pat. No. 4,320,116 discloses the basic ingredients for feed compositions for swine, piglets, and other animals. U.S. Pat. No. 3,778,508 discloses basal feed compositions for sheep and cattle. These patents are incorporated herein by reference. Many other such compositions are well known to those skilled in the art.

Estriol according to the present invention is admixed with the feed in amounts sufficient to supply from about 0.01–4.0 mg/ruminant/day, typically 1.5–12 grams estriol/ton of feed, to the ruminant.

Estriol according to the present invention can be administered to the ruminants in a composition comprising an injectable formulation containing any biocompatible and estriol compatible carrier such as various vehicles, adjuvants, additives, and diluents.

Estriol is added to the carrier in amounts sufficient to supply from about 0.01–4.0 mg to the ruminants when injected. Preferably, estriol is added to the carrier in amounts sufficient to supply from about 0.05–2.0 mg/ruminant.

Nonaqueous vehicles such as cottonseed oil, sesame oil, olive oil, soybean oil, corn oil, sunflower oil, or peanut oil and esters such as isopropyl myristate may also be used as solvent systems for estriol compositions. Additionally, various additives which enhance the stability, sterility, and isotonicity of the composition including antimicrobial preservatives, antioxidants, chelating agents, and buffers can be added. Any vehicle, diluent, or additive used would, however, have to be compatible with estriol according to the present invention. Preferably, estriol is administered to the ruminant in an oleaginous vehicle consisting of olive oil, acetone, and benzyl alcohol, most preferably about 96% v/v olive oil, about 3% v/v acetone, and about 1% v/v benzyl alcohol.

Estriol according to the present invention can be administered to the ruminants in the form of a slow-release subcutaneous implant which is inserted beneath the skin, preferably the ear. The implant can take the form of a pellet which slowly dissolves after being implanted or a biocompatible and ruminant compatible delivery module well known to those skilled in the art. Such well known dosage forms and modules are designed such that the active ingredients are slowly released over a period of several days to several weeks. Examples of well known implants and modules useful in the present invention include: U.S. Pat. No. 4,487,603 discloses an implantable micro-infusion pump for dispensing medication at a controlled rate. U.S. Pat. No. 4,486,194 discloses a therapeutic device for administering medicants through the skin. U.S. Pat. No. 4,447,233 discloses a medication infusion pump for delivering medication at a precise infusion rate. U.S. Pat. No. 4,447,224 discloses a variable flow implantable infusion apparatus for continuous drug delivery. U.S. Pat. No. 4,439,196 discloses an osmotic drug delivery system having multi-chamber compartments. U.S. Pat. No. 4,475,196 discloses an osmotic drug delivery system. These patents are incorporated herein by reference. Many other such implants and modules are well known to those skilled in the art.

The implant, pellet or module, according to the present invention is designed to deliver estriol in amounts from about 0.01–4.0 mg/ruminant/day, preferably from about 0.05–2 mg/ruminant/day.

Estriol can be administered to any ruminant, particularly cattle and sheep, to promote growth and increase feed utilization efficiency.

According to the present invention, a composition for promoting growth and increasing feed utilization efficiency in ruminants comprises a pharmaceutically acceptable carrier and a growth promoting and feed utilization efficiency increasing amount of estriol admixed with the carrier. The composition of the present invention contains estriol in amounts sufficient to supply from about 0.01–4.0 mg estriol/ruminant/day. The composition can be in a form suitable for oral administration wherein the carrier is one of the following: tablets, suspensions, solutions, emulsions, capsules, powders, syrups, boluses, feed compositions, and the like. Preferably, the composition according to the present invention is a feed composition comprising a nutritionally balanced feed and a growth promoting and feed utilization efficiency increasing amount of estriol admixed with said feed.

Additionally, the composition according to the present invention can be in the form of an implant pellet comprising a biocompatible and estriol-compatible implant material and a growth promoting and feed utilization efficiency increasing amount of estriol or in the form of an injectable formulation comprising a biocompatible and estriol-compatible carrier and a growth promoting and feed utilization efficiency amount of estriol.

The invention having been generally described, the following examples are given as particular embodiments of the invention and to demonstrate the practice and advantages thereof. It is understood that the examples are given by way of illustration and are not intended to limit the specification or the claims to follow in any manner.

IN VIVO EXPERIMENTAL PROCEDURE

A 56-day lamb growth trial was conducted to evaluate the effects of estriol on rate of gain, feed efficiency and concentrations of urea in blood serum of growing/finishing wether lambs.

Forty-eight (48) spring-born wether lambs that were 3 to 4 months of age were used for the study. The lambs were born of Rambouillet ewes and were sired by Suffolk or Dorset rams. The lambs were housed indoors and in individual, raised wooden pens (1.22 M × 1.52 M) with slotted floors. Two days after arrival the lambs were vaccinated with *Clostridium perfringens* type D toxoid and were treated for internal parasites with levamisol hydrochloride. After a 12-day adaptation period to the facilities and starting ration, the lambs were blocked by breed and weight and were randomly assigned to treatments as follows: 1. Placebo (vehicle only); 2. estriol, 0.2 mg/ruminant/day; 3. estriol, 0.4 mg/ruminant/day; and 4. estriol, 0.8 mg/ruminant/day. Estriol was purchased from Berlichem, Inc. in Fort Wayne, N.J.

Mean initial weight of the lambs was 26.23 kg. On days 14 and 21 of the study, respectively, all lambs were given a booster vaccination of *Clostridium perfringens* type D toxoid, and were retreated for internal parasites with fenbendazole.

The lambs were identified by numbered ear tags that were color-coded according to treatment. The experimental compounds were dissolved into an oleaginous vehicle consisting of olive oil (95.8% v/v), acetone (3.1% v/v) and benzyl alcohol (1.1% v/v). Each week new solutions were prepared in amounts sufficient to last one week, aliquots of each solution were saved for analysis of the experimental compounds, and the solutions were stored in glass serum bottles with rubber serum stoppers in the refrigerator when not being used. Treatments were given by daily subcutaneous injections of 1.0 ml per lamb in the scapular region with 18 gauge needles. The lambs were shorn over the scapular region during the adaptation period, and a new sterile needle was used for each injection. Injections were made each day between 0900 and 1100 hours, and were altered between the left and right sides of the lambs.

Lambs had ad libitum access throughout the study to water and either the start or finish rations as shown in Table 1. Fresh feed was added daily to each feeder. The start and finish rations contained (dry matter (DM) basis), respectively, about 58 and 69% ground corn and calculated crude protein contents of 15.0 and 12.5%. The rations were pelleted (3/16 inch), and samples were taken weekly for analysis of dry matter (DM) and crude protein. Feeders of each lamb were emptied weekly, and orts were weighed and discarded.

Blood samples were taken by jugular puncture from each lamb on days 25 and 53. The blood was allowed to clot in vacutainer tubes for one hour at room temperature or until the clot began to retract from the wall of the tube. Serum was separated by centrifugation, and frozen at $-20°$ C. until analyzed for urea-N by the Tiffany et al. modification of Talke and Schubert enzymatic method. See, Talke and Schubert, *Klin. Wochenschr.*, 43:174 (1965). and Tiffany et al., *Clin. Chem.*, 18:829 (1972).

The data were analyzed by analysis of variance for a randomized complete block design using the General Linear Model procedure of the Statistical Analysis System (SAS), available commercially from SAS Institute, Inc. in Cary N.C. The model included effects of treatment and block, and the linear effects of estriol were evaluated. Data of 3 lambs was deleted as being statistical outliers. The final data set consisted of 11, 12, 11, and 11 lambs for treatments 1-4, respectively. The results are shown in Tables 2 and 3.

Referring to Table 2, estriol increased the average daily gain (ADG) and improved the feed/gain ratio compared to the animals which did not receive estriol. Weight gains of lambs increased linearly for the trial ($P<0.01$) in response to increasing dosages of estriol. Estriol had no effect ($P>0.05$) on feed intake. Feed efficiency was also improved linearly ($P<0.01$) during the trial.

Referring to Table 3, estriol decreased the blood urea nitrogen (BUN) concentrations at both blood sampling intervals, with a significant ($P<0.05$) linear effect observed at day 25. The BUN data support the observation that estriol improved the rate of weight gain and feed efficiency of these lambs.

Obviously many modifications and variations of the present invention are possible in light of the above teachings. It is therefore to be understood that within the scope of the appended claims the invention may be practiced otherwise than as specifically described.

TABLE 1

Ingredient and Calculated Nutrient Composition (DM Basis) of Start and Finish Rations

| Item | Start | Finish |
|---|---|---|
| Ingredient | % | % |
| Corn, ground | 58.42 | 69.38 |
| Cottonseed hulls | 14.00 | 11.72 |
| Soybean meal | 11.58 | 7.00 |
| Sugarcane molasses | 4.00 | 4.00 |
| Dehydrated alfalfa meal | 6.25 | 3.75 |
| Cottonseed meal | 3.75 | 2.25 |
| Ground limestone | 1.5 | 1.40 |
| Plain salt | .35 | .35 |
| Trace-mineralized salt | .15 | .15 |
| Vitamin premix[a] | | |
| Calculated composition | | |
| NE maintenance, Mcal/cwt | 81.87 | 84.52 |
| NE gain, Mcal/cwt | 55.60 | 58.47 |
| Crude protein, % | 14.96[b] | 12.50[c] |
| Calcium, % | .78 | .69 |
| Phosphorus, % | .36 | .34 |
| Potassium, % | .95 | .77 |

[a]To supply 1000, 125 and 0.05 IU of vitamins A, D and E, respectively, per pound of ration (as-fed).
[b]Mean crude protein content of two separate batches was 15.4% (n = 3) and 17.1% (n = 2) by analysis.
[c]Mean crude protein content by analysis was 11.8% (n = 3).
NE = Net Energy
Mcal/cwt = Megacalories per hundred weight of feed
IU = International units

TABLE 2

Least Squares Means for Sheep Performance Data

| | Estriol mg/ruminant/day | | | |
|---|---|---|---|---|
| | 0 | 0.2 | 0.4 | 0.8 |
| Days 1-56 | | | | |
| Gain,kg/day[a] | 0.26 | 0.27 | 0.30** | 0.29* |
| Feed,kg/day | 1.35 | 1.37 | 1.40 | 1.37 |
| Feed/gain[a] | 5.32 | 5.22 | 4.71* | 4.71* |

Differs from placebo (0 mg/ruminant): *$P < .05$ **$P < .01$.
[a]Significant linear response ($P < .01$).

TABLE 3

Least Squares Means for Sheep Performance Data

| | Estriol mg/ruminant/day | | | |
|---|---|---|---|---|
| | 0 | 0.2 | 0.4 | 0.8 |
| BUNs, mg/dl | | | | |
| Day 25[a] | 26.0 | 19.6** | 24.2 | 18.9** |
| Day 53 | 12.3 | 9.2* | 10.5 | 9.9 |

Differs from placebo (0 mg/ruminant): *$P < .05$ $P < .01$ *$P < .001$.
P = probability value or significance level (probability of concluding a treatment effect when in reality a treatment effect doesn't exist).
[a]Significant linear response ($P < .05$).

What is claimed is:

1. A method for promoting growth and increasing feed utilization efficiency in ruminants, comprising:
    administering a growth promoting and feed utilization efficiency increasing amount of estriol to said ruminants.

2. A composition for promoting growth and increasing feed utilization efficiency in ruminants, comprising:
    a pharmaceutically acceptable carrier; and
    a growth promoting and feed utilization efficiency increasing amount of estriol.

3. The method of claim 1 wherein estriol is administered parenterally.

4. The method of claim 3 wherein estriol is administered using an implant, said implant further comprising:

a biopatible and estriol compatible implant material; and a growth promoting and feed utilization efficiency increasing amount of estriol.

5. The method of claim 3 wherein estriol is administered in an injectable formulation, said injectable formulation further comprising:

a biocompatible and estriol compatible carrier; and a growth promoting and feed utilization efficiency increasing amount of estriol.

6. The method of claim 1 wherein estriol is administered orally.

7. The method of claim 6 wherein said oral method selected from the group consisting of administering estriol to said ruminants in tablets, suspensions, solutions, emulsions, capsules, powders, syrups, boluses, and feed compositions.

8. The method of claim 7 wherein estriol is administered in a feed composition, said feed composition further comprising:

a nutritionally balanced feed; and a growth promoting and feed utilization efficiency increasing amount of estriol admixed with said feed.

9. The method of claim 1 wherein said ruminants are selected from the group consisting of cattle and sheep.

10. The composition of claim 2 in the form of an oral composition.

11. The composition of claim 10 in the form of an oral composition selected from the group consisting of tablets, suspensions, solutions, emulsions, capsules, powders, syrups, boluses, and feed compositions.

12. The composition of claim 2 in a form suitable for parenteral administration.

13. The composition of claim 12 in the form of an implant, said implant further comprising:

a biocompatible and estriol compatible implant material; and a feed utilization efficiency promoting growth and increasing amount of estriol.

14. The composition of claim 12 in the form of an injectable formulation, said injectable formulation further comprising:

a biocompatible and estriol compatible carrier; and a feed utilization efficiency promoting growth and increasing amount of estriol.

15. The oral composition of claim 11 in the form of a feed composition, said feed composition further comprising:

a nutritionally balanced feed; and a growth promoting and feed utilization efficiency promoting growth and increasing amount of estriol admixed with said feed.

16. The feed composition of claim 15 containing about 1.5–12 grams estriol/ton of feed.

* * * * *